(12) United States Patent
Griese et al.

(10) Patent No.: US 10,238,108 B2
(45) Date of Patent: *Mar. 26, 2019

(54) ACIDIC BIOFILM REMEDIATION

(71) Applicant: ECOLAB USA INC, Saint Paul, MN (US)

(72) Inventors: Gregory G. Griese, Saint Paul, MN (US); Mark Levitt, Saint Paul, MN (US); Richard K. Staub, Saint Paul, MN (US); Stefanie Gilbreth, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/110,821

(22) Filed: Aug. 23, 2018

(65) Prior Publication Data

US 2018/0360036 A1    Dec. 20, 2018

Related U.S. Application Data

(63) Continuation of application No. 13/045,734, filed on Mar. 11, 2011, now Pat. No. 10,085,447.

(51) Int. Cl.
   *A01N 41/04*  (2006.01)

(52) U.S. Cl.
   CPC .................................. *A01N 41/04* (2013.01)

(58) Field of Classification Search
   CPC .......................................................... A01N 41/04
   See application file for complete search history.

(56) References Cited

U.S. PATENT DOCUMENTS

| | | | |
|---|---|---|---|
| 3,882,038 A | 5/1975 | Clayton et al. | |
| 5,080,831 A | 1/1992 | VanEenam | |
| 5,143,720 A | 9/1992 | Lopes | |
| 6,593,283 B2 | 7/2003 | Hei et al. | |
| 6,699,825 B2 | 3/2004 | Rees et al. | |
| 6,767,881 B1 | 7/2004 | Griese et al. | |
| 6,812,196 B2 | 11/2004 | Rees et al. | |
| 6,846,793 B1 | 1/2005 | Griese | |
| 6,927,237 B2 | 8/2005 | Hei et al. | |
| 6,936,579 B2 | 8/2005 | Urban | |
| 7,186,676 B2 | 3/2007 | Boone et al. | |
| 2002/0168422 A1 | 11/2002 | Hei et al. | |
| 2005/0096245 A1 | 5/2005 | Hei et al. | |
| 2009/0184062 A1 | 7/2009 | Pickens | |
| 2009/0192327 A1 | 7/2009 | Eldridge et al. | |
| 2009/0202615 A1 | 8/2009 | Rodheaver et al. | |
| 2009/0214674 A1 | 8/2009 | Barraud | |
| 2009/0241991 A1 | 10/2009 | Vaillancourt et al. | |
| 2009/0253605 A1 | 10/2009 | Van Buskirk et al. | |
| 2009/0255536 A1 | 10/2009 | Av-Gay et al. | |
| 2009/0258086 A1 | 10/2009 | Myntti | |
| 2009/0263438 A1 | 10/2009 | Melander et al. | |
| 2009/0270475 A1 | 10/2009 | Melander et al. | |
| 2009/0275652 A1 | 11/2009 | Okano et al. | |
| 2009/0304621 A1 | 12/2009 | Cavitt et al. | |
| 2010/0004480 A1 | 1/2010 | Eldridge et al. | |
| 2010/0112728 A1 | 5/2010 | Korzenski et al. | |

FOREIGN PATENT DOCUMENTS

WO       9854277 A1    12/1998

OTHER PUBLICATIONS

Dow Chemical Company product information for DOWANOL DPnB, "A slow-evaporating, hydrophobic glycol ether with excellent surface tension-lowering ability and coalescing properties", pp. 1-2, 2012.

*Primary Examiner* — Peter F Godenschwager

(74) *Attorney, Agent, or Firm* — McKee, Voorhees & Sease, PLC

(57) ABSTRACT

Methods and compositions for biofilm remediation are disclosed. Biofilm is reduced and removed from soiled surfaces by providing to a surface in need an effective amount of a composition comprising a biocidal surfactant and at least one organic solvent. According to the invention, the biofilm remediation compositions reduce and remove biofilm formation by administering a one-step cleaner and disinfectant. The biofilm remediation compositions are stable and effective in concentrated and diluted ready-to-use formulations comprising an anionic sulfated or sulfonated surfactant that is not an organocarboxylic acid, a sparingly soluble organic solvent and optionally a soluble organic solvent.

20 Claims, No Drawings

ACIDIC BIOFILM REMEDIATION

CROSS-REFERENCE TO RELATED APPLICATION

This is a Continuation Application which claims priority to nonprovisional application U.S. Ser. No. 13/045,734, filed Mar. 11, 2011, which is herein incorporated by reference in its entirety.

FIELD OF THE INVENTION

The invention relates to the field of biofilm remediation, including the treatment of a variety of biofilm-soiled surfaces. More particularly, the invention relates to compositions, compounds, and methods for reducing and removing biofilm.

BACKGROUND OF THE INVENTION

Biofilms are biological conglomerates that contain pathogens, such as bacteria and other microorganisms, embedded in a matrix of exopolymers and macromolecules. In addition to bacteria, other microorganisms are commonly found in biofilm, including fungi, molds, algae, protozoa, archaea and mixtures of these microorganisms. Biofilms form as a result of microorganisms establishing on a surface and producing a protective extracellular polymeric matrix. Most often biofilm form on surfaces in contact with water, providing a hydrated matrix of polysaccharides to provide structural protection from biocides, making biofilm more difficult to kill than other pathogens.

Microbial infection and the formation of biofilm present significant complications in numerous industries. Although biofilm are known to exist in a wide-variety of environmental conditions, since biofilm most often form on surfaces exposed to bacteria and water, industries such as food processing are commonly affected by biofilm. For example, the organism *Listeria monocytogenes* thrives in cool, damp environments, such as floor drains, plumbing and other surfaces of food processing facilities. This provides a potential point of contamination for a processing plant environment and food products produced therein. However, biofilm can also develop on inert surfaces of everyday household items. Exposure to such microorganisms through skin-surface contact may result in infections and compromise the public's health. Therefore, controlling the formation of biofilm is desirable to decrease exposure to infectious microorganisms.

Biofilm growth and removal depends on several factors, including the surface composition and chemical composition of the surrounding environment. Several biofilm removal methods are utilized, including physical, chemical and biological removal. Means of physically removing biofilm include the use of magnetic fields, ultra sound, high and low electrical fields and abrasive techniques. Physical removal techniques are often combined with chemical or biological methods, such as biocides or antimicrobial agents. A number of technologies have been developed that treat surfaces with organic or inorganic materials to interfere with biofilm development, such as preventing microbial attack and degradation. For example, coating a surface with or incorporating a composition into a surface substrate to create a surface wherein microorganisms do not adhere or colonize. U.S. patent application Ser. No. 12/134,353. However, such technologies have not effectively eliminated biofilm formation and growth. Therefore, the contamination of surfaces with biofilm remains a problem.

In light of the foregoing, there remains a demand for compositions and methods for reducing and removing biofilm.

Accordingly, it is an objective of the claimed invention to develop improvements in biofilm remediation methods and compositions.

A further object of the invention is a method of biofilm remediation capable of cleaning and disinfecting a variety of surfaces.

A further object of the invention is the development of compositions for the effective remediation of biofilm.

BRIEF SUMMARY OF THE INVENTION

An embodiment of the invention is a method for reducing and removing biofilm by providing to a surface in need thereof an effective amount of a composition including a biocidal surfactant and at least one organic solvent at an acidic pH. In a preferred embodiment, the composition includes a biocidal anionic sulfated or sulfonated surfactant, a sparingly soluble organic solvent, and optionally a soluble organic solvent.

In another embodiment, the invention provides methods for reducing and removing biofilm in or on a hard surface, which comprises providing the surface in need thereof with an effective amount of one or more of the biofilm remediation compositions. The biofilm remediation compositions of the present invention reduce and remove biofilm formation by administering a one-step cleaner and disinfectant. The biofilm remediation compositions are stable and effective in concentrated forms and diluted ready-to-use solutions.

According to the invention, the biofilm remediation compositions provide synergistic reduction in biofilm concentration at neutral pH as well as pH <7. Embodiments of the invention disclose the synergistic combination of surfactant and solvent system to enable biocidal activity beyond the activity of the surfactant agent in the compositions of the invention.

DETAILED DESCRIPTION OF THE PREFERRED EMBODIMENT

The present invention pertains to the field of biofilm remediation. More particularly, the invention provides novel methods and compositions for reducing and removing biofilm formation on various surfaces.

The embodiments of this invention are not limited to particular methods and compositions for biofilm remediation, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "alkyl," as used herein, refers to a straight or branched chain monovalent hydrocarbon radical having a specified number of carbon atoms. Alkyl groups may be unsubstituted or substituted with substituents that do not interfere with the specified function of the composition and may be substituted once or twice with the same or different group. Substituents may include alkoxy, hydroxy, mercapto, amino, alkyl substituted amino, nitro, carboxy, carbanoyl, carbanoyloxy, cyano, methylsulfonylamino, or halo, for example. Examples of "alkyl" include, but are not limited to, methyl, ethyl, n-propyl, isopropyl, n-butyl, s-butyl, t-butyl, n-pentyl, n-hexyl, 3-methylpentyl, and the like.

The term "antimicrobial," as used herein, refers to the ability to kill or inhibit the growth of microorganisms. According to the invention, the compositions and methods of biofilm remediation in their broadest sense may differ from current governmental regulations, such as regulations for antimicrobial standards. Therefore, the use in connection with this invention of the term "antimicrobial" and the like is not intended to indicate compliance with any particular governmental standard for antimicrobial activity.

The term "aryl," as used herein, refers to monovalent unsaturated aromatic carbocyclic radicals having a single ring, such as phenyl, or multiple condensed rings, such as naphthyl or anthryl. Aryl groups may be unsubstituted or substituted with those substituents that do not interfere with the specified function of the composition. Aryl may be substituted by halo, $C_1$-$C_6$ alkyl, $C_1$-$C_6$ alkoxy, $C_2$-$C_6$ alkenyl, substituted $C_1$-$C_6$ alkyl, $C_1$-$C_6$ substituted alkoxy, substituted $C_2$-$C_6$ alkenyl, substituted alkoxy, amino, nitro, cyano, carboxy, hydroxymethyl, aminomethyl, carboxymethyl, $C_1$-$C_4$ alkylthio, hydroxy, $C_1$-$C_4$ alkanoyloxy, carbamoyl, or halo-substituted $C_1$-$C_6$ alkyl and may be substituted once or more with the same or different group. Such an aryl ring may be optionally fused to one or more of another heterocyclic ring(s), heteroaryl ring(s), aryl ring(s), or cycloalkyl rings. Examples of "aryl" include, but are not limited to, phenyl, 2-naphthyl, 1-naphthyl, biphenyl, 2-hydroxyphenyl, 2-aminophenyl, 2-methoxyphenyl and the like.

The term "biofilm," as used herein, means an extracellular matrix in which a population of microorganisms are dispersed and/or form colonies. Biofilms are understood to be typically made of polysaccharides and other macromolecules, often referred to as exopolysaccharides, that are concentrated at an interface (usually solid/liquid) and act as a binding agent that surrounds such populations of microorganisms. Biofilms are further understood to include complex associations of cells, extracellular products and detritus (or non-living particulate organic material) that are trapped within the biofilm or released from cells within the biofilm. The term biofilm, as used herein, further refers to the ASTM definition of biofilm as an accumulation of bacterial cells immobilized on a substratum and embedded in an organic polymer matrix of microbial origin. Biofilms are understood to be a dynamic, self-organized accumulation of microorganisms and microbial and environmental by-products that is determined by the environment in which it lives. According to the invention, the phrases "biofilm remediation," "removing biofilm," "reducing biofilm" and like phrases, shall mean the use of the chemical biocide according to the invention which causes a reduction in the rate or extent of biofilm growth, removal of existing biofilm or portions of biofilm on surfaces and/or eradication of existing biofilm on a treated surface. According to the invention, the biocidal compositions disclosed herein physically remove and kill biofilm.

The term "disinfectant," as used herein, refers to an agent that kills all vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15th Edition, 1990 (EPA Guideline 91-2).

The term "microorganism," as used herein, refers to any noncellular or unicellular (including colonial) organism. Microorganisms include all prokaryotes. Microorganisms include for example, bacteria (including cyanobacteria and Mycobacteria), lichens, microfungi, protozoa, virinos, viroids, viruses, and some algae. As used herein, the term "microbe" is synonymous with microorganism.

The term "sanitizer," as used herein, refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, against several test organisms.

The term "sparingly soluble," as used herein, refers to a second solvent that is soluble in a first solvent to an extent of less than about 20 wt-%, preferably less than about 10 wt-%, preferably less than about 5 wt-%, preferably less than about 3 wt-%. For example, a second solvent that is sparingly soluble in a first solvent can be soluble to an extent of 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, 0.2, or 0.1 wt-%, to less than any of these weight percentages, to any of these weight percentages modified by about, or to less than any of these weight percentages modified by about.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

As used herein, the differentiation of antimicrobial "-cidal" or "-static" activity are definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbicidal and the later, microbistatic. A sanitizer and a disinfectant are, by definition, agents which provide antimicrobial or microbicidal activity.

The biofilm remediation methods and compositions according to the embodiments of the invention present a significant improvement in the prior art and represent a significant change for industries in need of cleaning and sanitizing products for biofilm. The biofilm remediation methods and compositions according to the invention obviate the need for numerous biofilm-reducing agents that are individually and/or in combination unable to completely remove and/or kill biofilm. The biofilm remediation compositions according to the invention provide a superior biocidal product, resulting in improved kill rates of biofilm over known methods of chemical and biological removal or reduction. This is a beneficial result of the biofilm remediation compositions according to the invention having a "kill mechanism" capable of penetrating all layers of a biofilm composition and reaching the substrate surface. These and other benefits of the biofilm remediation methods and compositions according to the invention will be readily apparent based on the description contained here, providing improved compositions and methods for treating ubiquitous biofilm.

Various biofilm-reducing agents are known to provide some beneficial effects in biofilm reduction and/or prevention. For example, chelating agents such as EDTA and EGTA, chlorine, iodine and hydrogen peroxide have previously been used as biofilm-reducing agents. Chelating agents destabilize the outer cell membrane of the biofilm. Chlorine, iodine, and hydrogen peroxide remove biofilm by depolymerizing the matrix. Further, biofilm-reducing agents may include antimicrobial proteins, such as nisin, which may be produced by *Lactococcus lactus*. Biocides or antimicrobial agents are also used as biofilm-reducing agents. Examples of biocides or antimicrobial agents that are effective include: iodophores; phenols including halo- and nitrophenols and substituted bisphenols such as 4-hexylresorcinol,2-benzyl-4-chlorophenol and 2,4,4'-trichloro-2'-hydroxydiphenyl ether; quaternary ammonium compounds and other cationic compounds; cationic surfactants such as alkyl and benzyl quaternary compounds like N-alkyl ($C_{12}$-$C_{18}$) dimethylbenzyl ammonium chloride monohydrate, dimethyl didecyl ammonium chloride, and N-alkyl and ($C_{12}$-$C_{14}$) dimethyl I-napthylmethyl ammonium chloride; organic and inorganic acids and its esters and salts such as dehydroacetic acid, peroxycarboxylic acids, peroxyacetic acid, methyl p-hydroxy benzoic acid; aldehydes such as glutaraldehyde; antimicrobial dyes such as is acridines, triphenylmethane dyes and quinones and halogens.

However, as described according to the invention, the biofilm remediation compositions and methods described herein provide enhanced antimicrobial "-cidal" mechanisms that are superior over prior biofilm-reducing agents. According to a preferred embodiment, the biofilm remediation composition and methods provide up to a 5-log order reduction in the population of microorganisms and pathogens in biofilm, compared to the optimal 3-log order reduction observed with use of the biofilm-reducing agents described above. The beneficial results of the biofilm remediation composition according to the invention result from the composition's penetration of all layers of a biofilm to the substrate surface, providing a complete kill of the microorganisms housed in such biofilm.

Compositions

Compositions according to the present invention were evaluated and demonstrated to provide advantageous remediation of biofilm. According to an embodiment of the invention, a biofilm remediation composition may comprise from about 0.1 to about 90 wt-% of an anionic surfactant and from about 0.1 to about 60 wt-% of a sparingly soluble organic solvent. The biofilm remediation composition may further contain from about 0.1 to about 60 wt-% of a soluble organic solvent. According to the invention, the anionic surfactant is a sulfonated acid and the composition has a pH of less than about 5. According to a further embodiment of the invention, the anionic surfactant is a sulfonated acid and the composition has a pH of less than about 4, and preferably less than about 3.5.

According to another embodiment of the invention, the biofilm remediation composition may comprise from about 5 to about 90 wt-% of an anionic surfactant and from about 5 to about 50 wt-% of a sparingly soluble organic solvent. The biofilm remediation composition may further comprise from about 5 to about 50 wt-% of a soluble organic solvent. According to this embodiment of the invention, the anionic surfactant may be a sulfonated acid and the composition may have a pH of less than about 5. According to a further embodiment of the invention, the anionic surfactant is a sulfonated acid and the composition has a pH of less than about 4, and preferably less than about 3.5.

According to a still further embodiment of the invention, the biofilm remediation composition comprises from about 10 to about 80 wt-% of an anionic surfactant, from about 15 to about 45 wt-% of a sparingly soluble organic solvent, and optionally from about 15 to about 45 wt-% of a soluble organic solvent. According to this embodiment of the invention, the anionic surfactant may be a sulfonated acid and the composition may have a pH of less than about 5. According to a further embodiment of the invention, the anionic surfactant is a sulfonated acid and the composition has a pH of less than about 4, and preferably less than about 3.5.

According to a further embodiment of the invention, a concentrated biofilm remediation composition may comprise from about 0.5 to about 30 wt-% of an anionic surfactant, from about 0.1 to about 10 wt-% of a soluble organic solvent and from about 0.5 to about 40 wt-% of a sparingly soluble organic solvent. According to a preferred embodiment, a ready-to-use biofilm remediation composition may comprise from about 0.2 to about 2 wt-% of an anionic surfactant and from about 0.5 to about 5 wt-% of a sparingly soluble organic solvent in dilution.

According to a still further embodiment of the invention, a diluted ready-to-use biofilm remediation composition comprises the concentrated composition of the anionic surfactant, sparingly soluble organic solvent and soluble organic solvent, diluted with water. According to a preferred embodiment the dilution is about 5 parts water per 1 part concentrated composition to about 128 parts water per 1 part concentrated composition. According to a further embodiment the dilution is from about 8 parts water per 1 part concentrated composition to about 64 parts water per 1 part concentrated composition. According to a still further embodiment the dilution is from about 32 parts water per 1 part concentrated composition.

Surprisingly, the biofilm remediation compositions according to the invention are efficacious against both gram positive and gram negative bacteria across a broad range of pH. According to an embodiment of the invention, the biofilm remediation compositions provide gram positive and gram negative sanitizing effects at pH ranges from about 0 to 10, 1 to 9, 2 to 8, and preferably from about 3 to 7. According to a preferred embodiment, the pH of a biofilm remediation composition is less than about 7, less than about 6, less than about 5, less than about 4, less than about 3.5, less than about 3, less than about 2 or less than about 1.

Surfactants

Surfactants are incorporated in the present biofilm remediation compositions. According to the invention, the biofilm remediation composition comprises a surfactant providing biocidal activity. According to a preferred embodiment of the invention, the biofilm remediation composition comprising a biocidal surfactant has a pH less than about 8. According to a preferred embodiment, the biofilm remediation composition has a pH of less than about 7, preferably less than about 6, more preferably less than about 5, and still more preferably a pH between about 1 and about 4. According to a most preferred embodiment, the biofilm remediation composition comprising the surfactant has an acidic pH between about 2 and about 4. Although not intending to be limited to a particular theory as to the nature of the cleaning and disinfecting properties of the biofilm remediation composition, the acidic pH of the composition comprising the surfactant promotes the protonation of the surfactant to provide biocidal activity, rather than detergent activity in alkaline conditions.

Suitable surfactants for use in the acidic biofilm remediation composition of the invention, include anionic surfactants or surface-active agents, sulfated surfactants or surface-active agents, sulfonated surfactants or surface-active agents and/or any combinations thereof. The surfactant according to the invention may be a single surfactant or surface-active agent or combinations of surfactants and/or surface-active agents.

Anionic surfactants may include, for example, sulfonates and surface active sulfonates, such as sulfonated acids, and sulfates. Suitable sulfonates may include, for example, alkylsulfonates, alkylbenzenesulfonates, alkylarylsulfonates, diphenylated sulfonates, such as alkylated diphenyl oxide disulfonate, secondary alkane sulfonate, sulfonated fatty acid esters, sulfonated acids, and the like. Sulfonated acids may include, for example, xylene sulfonic acid, sulfonated oleic acid (also referred to as oleic acid sulfonates) and the like. Suitable sulfates may include, for example, sulfated alcohols, sulfated alcohol ethoxylates, sulfated alkylphenols, alkylsulfates, sulfosuccinates, alkylether sulfates, alkyl sulfates, linear and branched primary and secondary alkyl sulfates, alkyl ethoxysulfates, fatty oleyl glycerol sulfates, alkyl phenol ethylene oxide ether sulfates and the like. Numerous suitable surfactants according to the invention are commercially available, for example, as Steppen PC-48™ (sulfonated fatty acid methyl ester).

According to a further embodiment, suitable synthetic, water soluble anionic surfactants may include the ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from about 5 to about 18 carbon atoms in the alkyl group in a straight or branched chain, e.g., the salts of alkyl benzene sulfonates or of alkyl toluene, xylene, cumene and phenol sulfonates; alkyl naphthalene sulfonate, diamyl naphthalene sulfonate, and dinonyl naphthalene sulfonate and alkoxylated derivatives or their free acids. Suitable sulfonates include olefin sulfonates, such as long chain alkene sulfonates, long chain hydroxyalkane sulfonates or mixtures of alkenesulfonates and hydroxyalkane-sulfonates. Suitable sulfonates include secondary alkane sulfonates.

According to a preferred embodiment, an alkylsufonate is the surfactant, preferably a ($C_8$-$C_{22}$) alkylsufonate surfactant, more preferably a ($C_{10}$-$C_{22}$) alkylsufonate surfactant. According to an alternative preferred embodiment, the sulfonates surfactant is a linear alkyl benzene sulfonic acid (LAS) providing sufficient biocidal activity for biofilm remediation and further solubilizing the sparingly soluble solvent of the composition. According to the invention, the surfactant, such as in a preferred embodiment using LAS is most effective at pH 3.0 or below due to the protonated chemistry of the surfactant. In addition, the surfactant according to the invention is most effective in combination with the solvent components as described herein.

As will be apparent to those skilled in the art, the above-listed surfactants are illustrative and various other surfactants meeting the criteria set out above may also be used according to the invention.

According to an embodiment of the invention, the surfactants exclude short chain (C1-C5) organocarboxylic acids. In particular, alpha- and beta-hydroxycarboxylic acids, such as lactic acid and glycolic acid are not selected as surfactants according to the biofilm remediation compositions of the invention.

According to an embodiment of the invention, medium or long chain organocarboxylic acids are used as surfactants for the biofilm remediation compositions. These include, but are not limited to C6-C10 organocarboxylic acids, including for example, caproic, capric and caprylic acid). Additional suitable medium or long chain organocarboxylic acids include pelargonic and enanthic acids.

Soluble and Sparingly Soluble Organic Solvents

According to the invention, the biofilm remediation composition comprises at least one soluble and/or sparingly soluble organic solvent. The invention preferably comprises a two solvent biofilm remediation composition. The two solvent compositions preferably contain a first soluble organic solvent and a second solvent that is only sparingly soluble in the first solvent. According to the preferred embodiment of the invention, the two solvent biofilm remediation composition first contains a diluting solvent (e.g., organic solvent). The soluble organic solvent according to the invention is a hydrophilic (water soluble), miscible organic solvent. A suitable soluble organic solvent according to the invention keeps the composition's clarity and low viscosity to aid in forming and maintaining an easily dispensable biofilm remediation composition. According to a further embodiment, the soluble organic solvent maintains a second sparingly soluble organic solvent in solution.

According to the preferred embodiment of the invention, the biofilm remediation composition further contains a sparingly soluble organic solvent. According to an embodiment of the invention, the sparingly soluble organic solvent aids the biocidal surfactant in penetrating the multiple biofilm layers, rather only penetrating a monolayer of a traditional non-biofilm soil. One skilled in the art can further ascertain that the biofilm remediation composition may further comprise additional solvents and/or cosolvents, such as alcohols. One skilled in the art further understands that the solvents utilized according to the invention do not degrade the biocidal surfactant or other solvents of the composition.

Suitable soluble organic solvents and sparingly soluble organic solvents according to the invention, include for example, glycol ethers or benzyl alcohol. Although not intending to be limited according to a particular theory for the effectiveness of the cleaning and disinfecting action of the biofilm remediation compositions, ether removes non-microbial soil and allows penetration of the biofilm layers to reach the substrate surface.

Suitable glycol ether solvents according to the invention, include, for example, diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether, propylene glycol phenyl ether and mixtures thereof. Numerous suitable solvents according to the invention are commercially available, including for example, as DOWANOL EPh™ from Dow Chemical Co. (ethylene glycol phenyl ether), as DOWANOL DPM™ from Dow Chemical Co. (dipropylene glycol methyl ether) and DOWANOL PPh™ from Dow Chemical Co. (propylene glycol phenyl ether).

According to a preferred embodiment of the invention, glycol ethers are used as soluble and sparingly soluble organic solvents. According to a more preferred embodiment, the soluble organic solvent of the biofilm remediation composition is dipropylene glycol methyl ether and the sparingly soluble organic solvent is propylene glycol phenyl ether. According to a more preferred embodiment the soluble and sparingly soluble organic solvents make a clear, low viscosity biofilm remediation composition upon dilution. A still further preferred embodiment of the composition according to the invention does not comprise an organocarboxylic acid in the composition.

Oxidizing Agent

According to an embodiment of the invention, an oxidizing agent may be further included in the biofilm remediation composition for biofilm removal, cleaning and/or disinfecting microorganisms. The present composition can include any of a variety of oxidizing agents, for example, hydrogen peroxide. Additional suitable oxidizing agents according to the invention, in addition to hydrogen peroxide, include for example, inorganic and organic peroxides, such as, salts of perborate, percarbonate, persulfate, perphosphate, persilicate, percarbonic acid, ozone and mixtures of the same.

According to a preferred embodiment, hydrogen peroxide or a hydrogen peroxide constituent may be included as an inorganic oxidizing agent. Hydrogen peroxide is commercially available at concentrations of 35%, 50%, 70%, and 90% in water, with the 35% being most commonly used. The present biofilm remediation compositions can include, for example, from about 0.01 wt-% to about 35 wt-% hydrogen peroxide or oxidizing agent, preferably from about less than 35 wt-% for concentrated biofilm remediation compositions and from about less than 5 wt-% for ready-to-use biofilm remediation compositions.

Water and Additional Agents

The compositions of the invention may further include water. Water may be present in the biofilm remediation composition from about 0.01 wt-% to about 90 wt-%. According to the invention, the compositions may further comprise additional agents or adjuvants, such as aesthetic enhancing agents (i.e., dye, perfume, etc.) and the like. Adjuvants and other additive ingredients will vary according to the precise formulation of the biofilm remediation composition and its intended methods of use and can be included in the compositions in any amount.

Methods of Making Biofilm Remediation Composition

The composition according to the embodiments of the invention can be prepared by conventional manufacturing processes and equipment. The compositions can be dispensed in packaging typically utilized for cleaning products. Additional variations and modifications of the embodiments of the invention will be readily ascertainable to those skilled in the art.

Methods of Biofilm Remediation

In an embodiment of the invention, the methods include applying the biofilm remediation compositions to a surface to reduce and/or eliminate biofilm. A method for biofilm remediation can include contacting a surface with the biofilm remediation composition. For example, the composition can be introduced to a hard surface in contact with biofilm, such as walls, floors, sinks, countertops and commercial food service surfaces According to the invention, the biofilm remediation methods inhibit biofilm by reducing and/or eliminating biofilm growth produced by a wide variety of bacteria and other microorganisms. For example, according to an embodiment of the invention, the methods for biofilm remediation are effective for biofilm comprising a variety of pathogens, such as both gram positive and negative bacteria, including for example

*Pseudomonas aeruginosa, Escherichia coli, Staphylococcus epidermidis, Staphylococcus aureus* and *Listeria monocytogenes.*

According to the invention, the biofilm remediation compositions described herein may be provided to a surface in contact with biofilm, by the application of the composition by wiping, spraying, dripping or the like. After applying the biofilm remediation composition to a surface, the composition can be allowed to contact the biofilm-soiled surface for a predetermined amount of time. The amount of time can be sufficient to allow the composition to penetrate the biofilm matrix. The method may comprise a single step of applying the solution onto the surface without direct physical removal, or may comprise both application and removal steps in order to physically remove the biofilm from the treated surface.

According to an embodiment of the invention, the population of microbes on or in a biofilm-soiled surface is reduced. The biofilm remediation methods of the invention provide greater than a 90% reduction (1-log order reduction) in the population of one or more biofilm microorganisms, such as *Pseudomonas*. More preferably, the methods provide a greater than 99% reduction (2-log order reduction) in such population. In a preferred embodiment, the invention provides a greater than 99.9% reduction (3-log order reduction) in the population of microorganisms and pathogens in biofilm. According to a more preferred embodiment, the invention provides a greater than 99.99% reduction (4-log order reduction) in such populations. A most preferred embodiment of the invention provides a greater than a 99.999% reduction (5-log order reduction) in the population of microorganisms and pathogens in biofilm.

According to the invention and the benefits described herein, the biofilm remediation compositions and methods of using the same are further useful in reducing the opportunity for gene transfer within biofilm due to the high kill rates in such populations. As a result of conjugation occurring at an increased rate in cells in biofilm, methods providing increased kill rates in the population of microorganisms and pathogens in biofilm, as demonstrated by up to a greater than 99.999% reduction (5-log order reduction), reduce gene transfer among such populations. Although not intending to be limited according to a particular theory, the methods of biofilm remediation according to the invention effectively reduce biofilm resistance to antimicrobials or chemical biocides, specifically for bacterium, as bacterial remediation reduces gene transfer of resistance to neighboring susceptible bacteria.

Treated Surfaces

According to some embodiments, the methods and compositions of the invention are applied to surfaces which are in need of cleaning and/or disinfecting, including, but not limited to those surfaces described in U.S. Pat. No. 7,569,232. According to the invention, a variety of inert surfaces where biofilm preferentially develops may be treated according to the methods of the invention, including surfaces of everyday and household items. Examples of such surfaces include, but are not limited to, hard surfaces, e.g., walls, floors, sinks, countertops and commercial food service surfaces. Additional surfaces that may be in need of cleaning and/or disinfecting according to the invention include surfaces exposed to dampness or water, such as those found in water and/ waste treatment, such as drain lines, pipes and other plumbing surfaces, tubes and valves and like. According to additional embodiments of the invention, exemplary industries in which the methods and compositions of the invention may be used include, but are not limited to, institutional industries, including hotels, housekeeping and foodservice; food processing; water care industries; janitorial industries; and health care.

The methods of the present invention may be used for microbial control, e.g., to reduce or remove biofilm formation and/or for cleaning and/or disinfecting of such surfaces. In certain embodiments, the biofilm remediation composition may be applied to the surface of a substrate that is susceptible to biofilm formation. The substrate may be made from any material to which such composition according to the invention may be applied. Representative examples of the kinds of materials from which the substrate may be made include porous materials, soft materials, hard materials, semi-hard materials, regenerating materials and non-regenerating materials. According to preferred embodiments of the invention, the substrate is a polymeric material (e.g., thermoplastic and thermoset), wood, metal, glass and ceramic, such as those materials found in the home and/or in public areas. Preferably, the substrate is made from an inert material selected from the group consisting of a polymer, a metal, an alloy, and combinations thereof.

According to an embodiment of the invention, the methods of biofilm remediation are used on a variety of surfaces in need of such treatment. The biofilm remediation compositions may be frequently applied to such surfaces, including as often as necessary to completely remove biofilm pathogens. The biofilm remediation compositions are compatible with a variety of treated surfaces permitting daily use without being corrosive to the treated surfaces. According to one embodiment, the biofilm remediation composition may be applied daily. As a result of the various treated surfaces being in contact with human tissue, for example in food or drink products or preparation, the control of unwanted biofilm requires the ongoing treatment of such surfaces and daily application, as permitted by the compatibility of the biofilm remediation composition according to the invention, provides a beneficial treatment frequency for a variety of surfaces.

Foaming Applications

According to an embodiment of the invention, the biofilm remediation compositions demonstrate enhanced surface retention time due to the foaming profile of the composition. As a result, application of the compositions according to the invention to a surface in contact with a biofilm can include administration of the composition to a drain or other surfaces in need of cleaning and/or disinfecting with a foaming chemistry. The biofilm remediation compositions are effective foaming chemistries suitable for administration into a trap to fill an entire void. A preferred embodiment of the invention is to administer the biofilm remediation composition to a drain in order to reduce and/or eliminate biofilm growing in the drain.

According to the invention, the biofilm remediation compositions described herein may be provided to a surface in contact with biofilm, such as a drain, by filling the drain or other void. After applying the biofilm remediation composition to the drain or other void, the composition remains in constant contact with the entire biofilm-soiled surface for a predetermined amount of time as a result of its preferred foaming profile. According to an embodiment of the invention, the biofilm remediation composition contacts the entire contaminated surface of the treated surface, rather than only covering the limited area wherein a liquid would contact and flow through. The amount of time for the interaction of the biofilm remediation composition with the biofilm-soiled surface is selected to be an amount of time sufficient to allow the composition to penetrate the biofilm matrix.

All publications and patent applications in this specification are indicative of the level of ordinary skill in the art to which this invention pertains. All publications and patent applications are herein incorporated by reference to the same extent as if each individual publication or patent application was specifically and individually indicated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

A formulation was created by combining the components in the amounts listed in the table below for an embodiment of the biofilm remediation composition.

| Component | Wt-% |
| --- | --- |
| Water | 43.4 |
| linear alkylbenzene sufonic acid | 19.2 |
| dipropylene glycol methyl ether | 5 |
| propylene glycol phenyl ether | 32.4 |

The removal of biofilm was tested to determine efficacy of biofilm removal and kill rates of *Pseudomonas aeruginosa*.

*Pseudomonas* are well-known as common 'pioneer' bacteria and often tested for biofilm-inhibiting agents' effectivity. The bacteria are known to excrete polysaccharides and generate biofilm on a variety of surfaces very rapidly (including, for example, stainless steel and polished hard surfaces), as well as commonly demonstrate resistance to various antimicrobial compositions. However, bacteria that exist in a biofilm are phenotypically different from suspended cells of the same genotype; therefore the study of biofilm in the laboratory requires protocols that account for this difference. Laboratory biofilms are engineered in growth reactors designed to produce a specific biofilm type. Altering system parameters correspondingly results in a change in the biofilm.

Standard ASTM test methods for the quantification of a *Pseudomonas aeruginosa* biofilm grown with high shear and continuous flow using a CDC biofilm reactor were followed (pursuant to ASTM Committee E-35 on Pesticides and Subcommittee E-35.15 on Antimicrobial Agents). This method was used to grow a repeatable *Pseudomonas aeruginosa* biofilm in a continuously stirred flow reactor with high wall shear. The method also provides instructions for sampling and analyzing biofilm for viable cells.

*Pseudomonas aeruginosa* (ATCC 700888) is the organism used. An isolated colony is aseptically removed from an R2A plate and placed into 100 ml of sterile bacterial liquid growth broth (300 mg/L) and incubated in an environmental shaker at 35° C.+2° C. for 20-24 hours. Viable bacterial density should equal 108 CFU/ml, and may be checked by serial dilution and plating. *Pseudomonas aeruginosa* were grown in a CDC reactor system for 48 hours at room temperature. See Goeres, D. M., et al., *Statistical assessment of a laboratory method for growing biofilms*, Microbiology 151:757-762 (2005). Biofilm challenge is approximately 8 logs throughout testing from a 48 hour growth.

Polycarbonate coupons were prepared. Coupons were removed from the rods, randomized and placed in containers where the biofilm remediation compositions were applied to the coupons in the containers for the specified exposure time (10 minutes). Coupons were then removed from the container and placed in tubes containing neutralizer. The samples are vortexed, sonicated, serially diluted and plated for plate counts. Biofilm population density was recorded as log colony forming units per surface area.

Example 2

A biofilm remediation composition according to the invention and disclosed below was tested for removal of biofilm and sanitizing efficacy was further tested to determine efficacy and kill rates against *Staphylococcus aureus* ATCC 6538 and *Pseudomonas aeruginosa* ATCC 15442 at both 30 second and 2.5 minute exposure times. The tests demonstrate sanitizing efficacy for inanimate, non-food contact surfaces.

| Desired Concentration | Diluent | Test Solution (Volume of Test Substance/Total Volume) | pH |
|---|---|---|---|
| 1:32 | 500 ppm Synthetic Hard Water (pH 7.66) | 6.25 g/500 g total | 2.11 |
| | | | 6.99* |

*pH adjusted with 1.0N NaOH.

The test systems used an inoculum volume of 20 µL; drying time/temperature of 30-40 minutes at 35° C.; ambient testing temperature (18-22° C.); exposure time of 30 seconds and 2.5 minutes; neutralizer media 20 mL Dey-Engley (DE) broth. A neutralizer screen was performed as part of the testing, verified that the neutralizer adequately neutralized the product and was not detrimental to the tested organisms. Plating Medium utilized was Tryptone Glucose Extract (TGE) agar and biofilm were incubated at 35° C. for 48 hours.

Results were analyzed according to the standard for non-food contact sanitizing efficacy screen (99.9% reduction in test organism growth is considered passing for a given exposure time).

Table 1 summarizes the average log growth of *Staphylococcus aureus* and *Pseudomonas aeruginosa* observed after a 30 second exposure to 1:32 biofilm remediation composition at its nominal pH and neutral pH 7.0. Test substances highlighted demonstrate reduction in the growth of *S. aureus* or *P. aeruginosa* by ≥99.9%, passing the non-food contact sanitizing efficacy screen.

TABLE 1

| Test System | Test Substance | Average $Log_{10}$ Survivors | Standard Deviation of Log Growth | Percent Reduction |
|---|---|---|---|---|
| *Staphylococcus aureus* ATCC 6538 | 1:32 Nominal pH | <1.40 | 0.00 | 100% |
| | 1:32 pH 7.0 | 5.00 | 0.11 | 99.137% |
| *Pseudomonas aeruginosa* ATCC 15442 | 1:32 Nominal pH | <1.40 | 0.00 | 99.999% |
| | 1:32 pH 7.0 | <1.40 | 0.00 | 99.999% |

Table 2 summarizes the average log growth of *Staphylococcus aureus* and *Pseudomonas aeruginosa* observed after a 2.5 minute exposure to 1:32 biofilm remediation composition at its nominal pH and pH 7.0 with highlighted substances according to the invention reducing the growth of *S. aureus* or *P. aeruginosa* by ≥99.9%.

TABLE 2

| Test System | Test Substance | Average $Log_{10}$ Survivors | Standard Deviation of Log Growth | Percent Reduction |
|---|---|---|---|---|
| *Staphylococcus aureus* ATCC 6538 | 1:32 Nominal pH | <1.40 | 0.00 | 100% |
| | 1:32 pH 7.0 | 4.00 | 0.14 | 99.893% |
| *Pseudomonas aeruginosa* ATCC 15442 | 1:32 Nominal pH | <1.40 | 0.00 | 99.973% |
| | 1:32 pH 7.0 | <2.39 | 1.71 | 99.997% |

The 1:32 dilutions of the biofilm remediation compositions according to the invention demonstrate efficacious sanitizing results for all compositions and treated biofilms at its nominal pH, as well as at a pH of 7.0 against *Pseudomonas aeruginosa* after both 30 seconds and 2.5 minutes. In addition, at its nominal pH, a 1:32 dilution of the biofilm remediation composition passed against *Staphylococcus aureus* with a 30 second and 2.5 minute exposure time. However, the results demonstrate an increase in solution pH has a negative impact on efficacy at least against *S. aureus*. At pH 7.0, the 1:32 dilution failed the non-food contact sanitizing screen after 30 seconds with a percent reduction of only 99.137%. Although the pH 7.0 passes the screen after 2.5 minutes, the percent reduction is 99.893%.

Example 3

A further biofilm remediation composition according to the invention and disclosed below was tested for removal of biofilm and sanitizing efficacy was tested according to the conditions set forth in Example 2 at a further dilution to determine efficacy and kill rates against *Staphylococcus aureus* ATCC 6538 and *Pseudomonas aeruginosa* ATCC 15442 at both 30 second and 2.5 minute exposure times. The tests demonstrate sanitizing efficacy for inanimate, non-food contact surfaces.

| Desired Concentration | Diluent | Test Solution (Volume of Test Substance/Total Volume) | pH |
|---|---|---|---|
| 1:64 | 500 ppm Synthetic Hard Water (pH 7.77) | 3.91 g/250 g total | 2.51 |
|  |  |  | 6.98* |

*pH adjusted with 1.0N NaOH.

Results were analyzed according to the standard for non-food contact sanitizing efficacy screen (99.9% reduction in test organism growth is considered passing for a given exposure time).

Table 3 summarizes the average log growth of *Staphylococcus aureus* and *Pseudomonas aeruginosa* observed after a 30 second exposure to 1:64 biofilm remediation composition at a nominal pH (2.51) and a neutral pH (6.98). Test substances highlighted demonstrate reduction in the growth of *S. aureus* or *P. aeruginosa* by ≥99.9%, passing the non-food contact sanitizing efficacy screen.

TABLE 3

| Test System | Test Substance | Average Log$_{10}$ Survivors | Standard Deviation of Log Growth | Percent Reduction |
|---|---|---|---|---|
| Staphylococcus aureus ATCC 6538 | 1:64 Nominal pH | 5.37 | 0.43 | 96.250% |
|  | 1:64 Neutral pH | 5.80 | 0.25 | 89.968% |
| Pseudomonas aeruginosa ATCC 15442 | 1:64 Nominal pH | 4.18 | 1.12 | 98.079% |
|  | 1:64 Neutral pH | 4.65 | 0.41 | 94.277% |

Table 4 summarizes the average log growth of *Staphylococcus aureus* and *Pseudomonas aeruginosa* observed after a 2.5 minute exposure to 1:64 biofilm remediation composition at its nominal pH and neutral pH with highlighted substances according to the invention reducing the growth of *S. aureus* or *P. aeruginosa* by ≥99.9%.

TABLE 4

| Test System | Test Substance | Average Log$_{10}$ Survivors | Standard Deviation of Log Growth | Percent Reduction |
|---|---|---|---|---|
| Staphylococcus aureus ATCC 6538 | 1:64 Nominal pH | 1.60 | 0.35 | 99.999% |
|  | 1:64 pH 7.0 | 5.18 | 0.13 | 97.564% |
| Pseudomonas aeruginosa ATCC 15442 | 1:32 Nominal pH | <1.40 | 0.00 | 99.997% |
|  | 1:32 pH 7.0 | 4.63 | 1.13 | 94.545% |

The 1:64 dilutions of the biofilm remediation compositions according to the invention demonstrate the most efficacious sanitizing results for a diluted biofilm composition at its nominal pH against *Pseudomonas aeruginosa* and *Staphylococcus aureus* after 2.5 minute exposure.

Although not intended to be limited to a particular theory or mechanism of action, the biofilm remediation compositions according to the invention demonstrate efficacious sanitizing results against both gram positive and gram negative bacteria at low pH (pH <5), according to this Example at a pH 2.51. However, the 1:64 diluted biofilm remediation compositions did not demonstrate the synergistic efficacy at a neutral pH—as achieved at the 1:32 dilution—as a result of the loss of activity from the combination of solvent and LAS. The dilution of the solvent demonstrates its partition into substrate (i.e. biofilm) occurring more quickly than the surfactant (showing a linear curve) even with dilution of the compositions. However, regardless of the dilution of the solvent system, the compositions demonstrate maintained efficacy against both gram negative bacteria (typical of biofilm) and gram positive bacteria provides an unexpected result achieved by the biofilm remediation compositions according to the invention.

Example 4

A non-food contact sanitizing efficacy test was conducted on ready-to-use samples of 4-in-1 biofilm remediation composition against *Pseudomonas aeruginosa* ATCC 15442. A 2.5 minute exposure time was utilized to test the sanitizing efficacy of compositions having a consistent amount of LAS surfactant and compositions having a gradient of solvent in order to observe whether or not the LAS surfactant provides the main source of efficacy. Table 5A shows the variation in the biofilm remediation compositions having decreasing amounts of solvent in the formulations.

TABLE 5A

| Composition | RM# | R012111A | R012111B | R012111C | R012111D |
|---|---|---|---|---|---|
|  |  | Percentage % | | | |
| Water | 100016 | 97.9800 | 98.1300 | 98.3300 | 98.4800 |
| LAS | 175075 | 0.6000 | 0.6000 | 0.6000 | 0.6000 |
| DPM | 164285 | 0.1600 | 0.1600 | 0.1600 | 0.1600 |
| PPh | 164048 | 1.0000 | 0.8500 | 0.6500 | 0.5000 |
| NaOH (50%) | 114132 | 0.2600 | 0.2600 | 0.2600 | 0.2600 |
| Total |  | 100.0000 | 100.0000 | 100.0000 | 100.0000 |
| pH |  | 7.0 | 7.0 | 7.0 | 7.0 |

The test systems used an inoculum volume of 20 μL; drying time/temperature of 30-40 minutes at 35° C.; ambient testing temperature (18-22° C.); exposure time of 2.5 minutes; neutralizer media 20 mL Dey-Engley (DE) broth. A neutralizer screen was performed as part of the testing, verified that the neutralizer adequately neutralized the product and was not detrimental to the tested organisms. Plating Medium utilized was Tryptone Glucose Extract (TGE) agar and biofilm were incubated at 35° C. for 48 hours.

Table 5B shows the results for the 2.5 minute exposure time of the biofilm remediation compositions having variations in solvent concentration.

TABLE 5B

| Test Substance | Rep | CFU/mL | CFU/Carrier* | Average Log Survivors | Geometric Mean | Percent Reduction |
|---|---|---|---|---|---|---|
| 4-in-1 Cleaner 1.0% PPh pH 7.0 | 1 | <$1.0 \times 10^0$ | <$2.5 \times 10^1$ | 2.98 | $9.6 \times 10^2$ | 99.893% |
| | 2 | $7.9 \times 10^1$ | $1.98 \times 10^3$ | | | |
| | 3 | $9.2 \times 10^1$ | $2.3 \times 10^3$ | | | |
| | 4 | $2.95 \times 10^2$ | $7.38 \times 10^3$ | | | |
| 4-in-1 Cleaner 0.85% PPh pH 7.0 | 1 | $1.7 \times 10^3$ | $4.25 \times 10^4$ | 4.58 | $3.84 \times 10^4$ | 95.728% |
| | 2 | $2.5 \times 10^3$ | $6.25 \times 10^4$ | | | |
| | 3 | $1.3 \times 10^3$ | $3.25 \times 10^4$ | | | |
| | 4 | $1.0 \times 10^3$ | $2.5 \times 10^4$ | | | |
| 4-in-1 Cleaner 0.65% PPh pH 7.0 | 1 | $6.0 \times 10^4$ | $1.5 \times 10^6$ | 6.37 | $2.36 \times 10^6$ | 0.000% |
| | 2 | $6.0 \times 10^4$ | $1.5 \times 10^6$ | | | |
| | 3 | $1.8 \times 10^5$ | $4.5 \times 10^6$ | | | |
| | 4 | $1.2 \times 10^5$ | $3.0 \times 10^6$ | | | |
| 4-in-1 Cleaner 0.50% PPh pH 7.0 | 1 | $1.0 \times 10^1$ | $2.5 \times 10^2$ | 5.17 | $1.49 \times 10^5$ | 83.426% |

Table 6 demonstrates the average log survivors of *Pseudomonas aeruginosa* ATCC 15442 observed after a 2.5 minute exposure to 4-in-1 cleaners at pH 7.0. The biofilm remediation composition with 1% solvent achieved a reduction of *P. aeruginosa* by ≥99.9%, and therefore have passed this non-food contact sanitizing efficacy screen after 2.5 minutes. As shown in Table 6, a decrease in the percent reduction of *P. aeruginosa* corresponds with the decrease of solvent in the composition even with a consistent level of LAS surfactant present.

TABLE 6

| Test System | Test Substance | Average Log$_{10}$ Survivors | Standard Deviation of Log Growth | Percent Reduction |
|---|---|---|---|---|
| *Pseudomonas aeruginosa* ATCC 15442 | 4-in-1 1.0% PPh | 2.98 | 1.08 | 99.893% |
| | 4-in-1 0.85% PPh | 4.58 | 0.17 | 95.728% |
| | 4-in-1 0.65% PPh | 6.37 | 0.23 | 0.000% |
| | 4-in-1 0.5% PPh | 5.17 | 1.86 | 83.426% |

The variation in solvency supports the synergy of the biofilm remediation composition according to the invention. As the tested biofilm remediation compositions in this Example were tested at a neutral pH were the base antimicrobial agent did not demonstrate a technical effect. The gradient of solvent (PPh) in the formulation showed at 1.0% a synergistic kill rate for the *P. aeruginosa*. The testing gradient further demonstrated a defined solvent effect loss moving from the 1.0% solvent to the 0.5% solvent concentration.

Example 5

Foaming stabilization of the biofilm remediation composition was analyzed to assess its foaming profile. As shown in Table 7, the 4 in 1 biofilm composition disclosed in Example 1 according to the invention was compared to various best in class foaming agents, including Pantastic, Scout and Oasis 135 (all commercially-available from Ecolab, Inc.) using the cylinder method. Initial foams for all products were spun for 4 minutes, using a 40 ml solution of each product.

TABLE 7

| Product | Concen. (oz/gal) | Temp. (° F.) | Initial Foam (mls) | Foam Height (mls) | | | |
|---|---|---|---|---|---|---|---|
| | | | | 2 minutes | 5 minutes | 7 minutes | 10 minutes |
| 4 in 1 | 1:32 | 110 | 250 | 250 | 250 | 220 | 190 |
| Pantastic | 1:32 | 110 | 250 | 250 | 250 | 250 | 210 |
| Scout | 1:32 | 110 | 250 | 250 | 250 | 250 | 250 |
| Oasis 135 | 1:32 | 110 | 250 | 250 | 250 | 230 | 200 |

As demonstrated in Table 7, the biofilm remediation composition provides comparable foaming characteristics to commercially-available high foaming products. The differences in foam height at 2 minutes, 5 minutes, 7 minutes and 10 minutes show results that are equal to or comparable to tested products. This foaming height achieved from the biofilm remediation composition is suitable for use in filling voids with constant contact of contaminated surfaces such as drain lines. The ability of a product to obtain this time of contact time in a void fill application directly leads to longer interaction of chemistry with bacteria on the surface. The foaming achieved by the biofilm remediation composition (and additional tested products) provides products having both an overall better coverage of surfaces as well as better cleaning and antimicrobial action as a result of the chemistries being in contact with the surfaces for sufficient periods of time.

Although not intended to be limited to a particular theory of the invention, the foaming activity of the biofilm remediation composition is directly related to a solvent effect of the formulation. As a result, the application of the biofilm remediation composition in a foaming liquid base system allows the solvent to be added in a cost effective manner that is more advantageous to the environment.

The inventions being thus described, it will be obvious that the same may be varied in many ways. Such variations are not to be regarded as a departure from the spirit and scope of the inventions and all such modifications are intended to be included within the scope of the following claims.

What is claimed is:

1. A method of biofilm remediation from a surface comprising:
   contacting a biofilm on the surface with a biocidal composition comprising
      from about 1 to about 30 wt-% of an anionic surfactant, wherein the anionic surfactant excludes short chain (C1-C5) organocarboxylic acid and is a sulfonated acid;
      from about 5 to about 25 wt-% of a soluble organic solvent; and
      from about 10 to about 40 wt-% of a sparingly soluble organic solvent;
      wherein the ratio of said soluble organic solvent to said sparingly soluble organic solvent is between about 10:1 and about 1:10 by weight percent;
      wherein said sparingly soluble organic solvent is soluble in the soluble organic solvent to an extent of less than about 20 wt-%;
      wherein the biocidal composition has a pH of less than about 3.5;
   wherein the biofilm comprises an extracellular matrix comprising polysaccharides and microbes.

2. The method of claim 1 wherein the anionic surfactant is selected from the group consisting of ($C_8$-$C_{22}$) alkylsulfonate, linear alkyl benzene sulfonic acid, diphenylated sulfonates, sulfonated oleic acid, and mixtures thereof.

3. The method of claim 1 wherein said sparingly soluble organic solvent is a glycol ether selected from the group consisting of benzyl alcohol, diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether, propylene glycol phenyl ether and mixtures thereof.

4. The method of claim 3, wherein the sparingly soluble and soluble organic solvents are a mixture of dipropylene glycol methyl ether and propylene glycol phenyl ether.

5. The method of claim 4 wherein the biocidal composition comprises between about 0.8 and 60 wt-% of dipropylene glycol methyl ether and between about 0.8 and 60 wt-% of propylene glycol phenyl ether.

6. The method of claim 1, wherein the biocidal composition further comprises between about 0.01 and about 35 wt. % of an oxidizing agent, wherein the oxidizing agent comprises hydrogen peroxide having an active concentration of 50% or greater; and wherein said anionic surfactant is from about 5 to about 25 wt-%.

7. The method of claim 6, wherein hydrogen peroxide has an active concentration of 70% or greater; and wherein the composition does not include a peroxycarboxylic acid or a halogen.

8. The method of claim 1 further comprising diluting the biocidal composition with water at a dilution ratio between about 5 parts water per 1 part biocidal composition and about 128 parts water per 1 part biocidal composition.

9. The method of claim 8 wherein the anionic surfactant is selected from the group consisting of ($C_8$-$C_{22}$) alkylsulfonate, linear alkyl benzene sulfonic acid, diphenylated sulfonates, sulfonated oleic acid, and mixtures thereof and wherein the sparingly soluble and soluble organic solvents are selected from the group consisting of benzyl alcohol, diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether, propylene glycol phenyl ether and mixtures thereof.

10. The method of claim 9 wherein soluble organic solvent and the sparingly soluble organic solvents are dipropylene glycol methyl ether and propylene glycol phenyl ether.

11. The method of claim 1 further comprising diluting the biocidal composition with water at a dilution ratio between about 16 parts water per 1 part biocidal composition and about 64 parts water per 1 part biocidal composition.

12. The method of claim 1 wherein the surface is a wall, a floor, a sink, a countertop, a drain, a drain line, a pipe, a tube, a valve, or a combination thereof.

13. The method of claim 1, wherein the microbes comprise one or more of a *Pseudomonas*, an *Escherichia*, a *Staphylococcus*, and/or a *Listeria*.

14. The method of claim 13, wherein the biocidal composition provides a 4-log order reduction of microbes on the biofilm-soiled surface.

15. A method of biofilm remediation from a surface comprising:
   contacting a biofilm on the surface with a biocidal composition comprising
      from about 0.1 to about 2 wt-% of an anionic surfactant, wherein the anionic surfactant is not a short chain (C1-5) organocarboxylic acid and is a sulfonated acid;
      from about 0.1 to about 2 wt-% of a soluble organic solvent in dilution; and
      from about 0.5 to about 5 wt-% of a sparingly soluble organic solvent in dilution;
      wherein the ratio of said soluble organic solvent to said sparingly soluble organic solvent is between about 10:1 and about 1:10 by weight percent;
      wherein said sparingly soluble organic solvent is soluble in the soluble organic solvent to an extent of about 15 wt-% or less; and
      wherein the biocidal composition has a pH of less than about 3;
   wherein the biofilm comprises an extracellular matrix comprising polysaccharides and microbes,
      wherein the microbes comprise one or more of a *Pseudomonas*, an *Escherichia*, a *Staphylococcus*, and/or a *Listeria*;
   wherein the biocidal composition provides a 3-log order reduction of microbes on the biofilm-soiled surface.

16. The method of claim 15 wherein the anionic surfactant is selected from the group consisting of ($C_8$-$C_{22}$) alkylsulfonate, linear alkyl benzene sulfonic acid, diphenylated sulfonates, sulfonated oleic acid, and mixtures thereof.

17. The method of claim 16 wherein the sparingly soluble organic solvent is selected from the group consisting of benzyl alcohol, diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether, propylene glycol phenyl ether and mixtures thereof.

18. The method of claim 17 wherein the sparingly soluble and soluble organic solvents are dipropylene glycol methyl ether and propylene glycol phenyl ether.

19. The method of claim 17, wherein the biocidal composition further comprises between about 0.01 and about 35 wt. % of an oxidizing agent, wherein the oxidizing agent comprises hydrogen peroxide having an active concentration of 70% or greater, and wherein the composition does not contain a peroxycarboxylic acid or a halogen.

20. The method of claim 19, wherein the biocidal composition provides a 4-log order reduction of microbes on the biofilm-soiled surface, and wherein the microbes comprise one or more of a *Pseudomonas aeruginosa*, a *Staphylococcus epidermidis*, a *Staphylococcus aureus*, a *Listeria monocytogenes*, and/or an *Escherichia coli*.

* * * * *